(12) United States Patent
Morita et al.

(10) Patent No.: US 11,338,153 B2
(45) Date of Patent: May 24, 2022

(54) PHOTOTHERAPEUTIC APPARATUS AND PROTOCOL SETTING METHOD FOR PHOTOTHERAPEUTIC APPARATUS

(71) Applicants: Inforward, inc, Tokyo (JP); Public University Corporation Nagoya City University, Nagoya (JP); SHIBUYA CORPORATION, Kanazawa (JP)

(72) Inventors: Akimichi Morita, Nagoya (JP); Katsutoshi Sakano, Kanazawa (JP)

(73) Assignees: INFORWARD, INC, Tokyo (JP); PUBLIC UNIVERSITY CORPORATION NAGOYA CITY UNIVERSITY, Nagoya (JP); SHIBUYA CORPORATION, Kanazawa (JP)

(*) Notice: Subject to any disclaimer, the term of this patent is extended or adjusted under 35 U.S.C. 154(b) by 457 days.

(21) Appl. No.: 16/387,006

(22) Filed: Apr. 17, 2019

(65) Prior Publication Data

US 2019/0321654 A1    Oct. 24, 2019

(30) Foreign Application Priority Data

Apr. 18, 2018 (JP) .............................. JP2018-080042

(51) Int. Cl.
*A61N 5/06* (2006.01)

(52) U.S. Cl.
CPC .......... *A61N 5/0616* (2013.01); *A61N 5/062* (2013.01); *A61N 2005/0643* (2013.01); *A61N 2005/0661* (2013.01)

(58) Field of Classification Search
CPC ...... A61N 5/06; A61N 5/0616; A61N 5/0618; A61N 5/062; A61N 5/0621; A61N 5/0624;
(Continued)

(56) References Cited

U.S. PATENT DOCUMENTS 6,221,095 B1 * 4/2001 Van Zuylen ......... A61N 5/0622
607/88
2013/0245724 A1 * 9/2013 Kaufman ............. A61N 5/0613
607/88

(Continued)

FOREIGN PATENT DOCUMENTS

JP      2002-032477 A    1/2002
JP      5497317 B2      10/2010
(Continued)

*Primary Examiner* — Ahmed M Farah
(74) *Attorney, Agent, or Firm* — Flynn Thiel, P.C.

(57) ABSTRACT

Provided is a phototherapeutic apparatus including: a probe that is held and operated by a user and provided with a photo-irradiation unit that performs irradiation with light beams; and a body provided with a control unit that controls the light beams. The body is provided with a read unit that reads a treatment protocol registered in an IC card (mobile memory medium), and a monitor (operation indication unit) that indicates a region to be irradiated with the light beams to the user, the region being set in the treatment protocol, and the control unit causes the monitor to indicate the region to be irradiated and causes the photo-irradiation unit to perform the irradiation with the light beams at a set value set in the treatment protocol. It is possible to perform the irradiation with the light beams in accordance with the treatment protocol and safely use the phototherapeutic apparatus.

5 Claims, 4 Drawing Sheets

(58) Field of Classification Search
CPC .... A61N 2005/0626; A61N 2005/0627; A61N 2005/0643; A61N 2005/0644; A61N 2005/065; A61N 2005/0658; A61N 2005/0661; A61N 2005/067; A61B 18/18; A61B 2018/1807; A61B 2018/202; A61B 18/203
USPC ...... 607/88–91, 94, 108; 606/9–13; 128/898
See application file for complete search history.

(56) References Cited

U.S. PATENT DOCUMENTS

| | | | |
|---|---|---|---|
| 2017/0215989 A1* | 8/2017 | Gregg, II | A61B 5/4547 |
| 2018/0154167 A1* | 6/2018 | Kim | G16H 20/70 |
| 2020/0105396 A1* | 4/2020 | Morita | G16H 20/40 |

FOREIGN PATENT DOCUMENTS

| | | | | |
|---|---|---|---|---|
| JP | 2017-164417 A | | 9/2017 | |
| WO | WO-2011109628 A1 * | | 9/2011 | ........... A61N 5/0616 |

* cited by examiner

PHOTOTHERAPEUTIC APPARATUS AND PROTOCOL SETTING METHOD FOR PHOTOTHERAPEUTIC APPARATUS

FIELD OF THE INVENTION

The present invention relates to a phototherapeutic apparatus and a protocol setting method for the phototherapeutic apparatus. More specifically, the present invention relates to a phototherapeutic apparatus that reads a treatment protocol in which a region to be irradiated with light beams and a set value of the light beams are set to irradiate light beams, and relates to a protocol setting method by which the set value of the treatment protocol of the phototherapeutic apparatus can be changed.

DESCRIPTION OF THE RELATED ART

There is hitherto known a phototherapeutic apparatus that irradiates an affected part with narrow-band ultraviolet B (UVB) light for the purpose of treating skin diseases such as psoriasis, vitiligo, or atopic dermatitis.

As an apparatus obtained by making such a phototherapeutic apparatus portable, there is known a phototherapeutic apparatus in which a photoirradiation unit is provided in a probe that can be held by a user (Japanese Patent Laid-Open No. 2017-164417).

Meanwhile, there is known a home treatment management system in which a patient is in advance given a medical examination by a medical doctor in a hospital, prescription data is recorded into an IC card based on the diagnosis, and an auto-peritoneal dialyzer or the like provided at home is caused to read the IC card, so that the operation of the auto-peritoneal dialyzer is controlled based on the prescription data (Japanese Patent No. 5497317).

Similarly, there is also known a home treatment management system in which an IC card with a program recorded therein is read into home medical equipment, measurement data or the like acquired by the home medical equipment is subjected to determination in accordance with a treatment adjustment program recorded in the IC card, to change treatment conditions of the home medical equipment (Japanese Patent Laid-Open No. 2002-32477).

SUMMARY OF THE INVENTION

By the way, the operator has to operate the probe to the affected part of the patient to be irradiated with light beams as in the phototherapeutic apparatus of Japanese Patent Laid-Open No. 2017-164417.

That is, in Japanese Patent No. 5497317 and Japanese Patent Laid-Open No. 2002-32477, the operation of the auto-peritoneal dialyzer and the treatment conditions of the home medical equipment are changed using the IC card, but the operation of the probe is not covered.

In view of such a problem, it is an object of the present invention to provide a phototherapeutic apparatus with improved safety, and a protocol setting method for the phototherapeutic apparatus which can change a set value of a treatment protocol for the phototherapeutic apparatus.

That is, a phototherapeutic apparatus according one aspect of the invention is a phototherapeutic apparatus including: a probe held and operated by a user; a photoirradiation unit that is provided in the probe and irradiates an affected part with light; and a body provided with a control unit that controls the light of the photo-irradiation unit. In the apparatus, the body is provided with a reader unit that reads a treatment protocol registered in a mobile memory medium, and an operation indication unit that indicates a region to be irradiated with the light to the user, the region being set in the read treatment protocol. The control unit causes the operation indication unit to indicate the region to be irradiated and causes the photo-irradiation unit to perform the irradiation with the light beams at a set value set in the treatment protocol.

Further, a protocol setting method for a phototherapeutic apparatus according to another aspect of the invention is a protocol setting method for a phototherapeutic apparatus that reads a treatment protocol, in which a set value of light is set, and performs irradiation with the light in accordance with the treatment protocol, the method including: transmitting an image showing a state of an affected part from a user to a medical institution; receiving the image in the medical institution; transmitting protocol change information from the medical institution to the user; receiving the protocol change information by the user; and changing the set value of the read treatment protocol based on the protocol change information.

According to a further aspect of the invention, the registered treatment protocol is read into the mobile memory media, and the operation indication unit indicates the region to be irradiated with light which is set in the treatment protocol, so that the user can accurately position the affected part on the probe in accordance with the indication.

Then, the irradiation with the light is performed at the set value set in the treatment protocol, whereby the affected part is appropriately irradiated with the light, and the user can thus perform the accurate treatment at home.

Further, in the medical institution, by preparation of the mobile memory media for each patient, it is possible to start treatment in accordance with the treatment protocol for each patient immediately after the patient visits the medical institution.

Moreover, according to yet another aspect of the invention, the treatment protocol can be changed based on the protocol change information transmitted from the medical institution, thereby enabling irradiation with light beams at an appropriate set value.

DETAILED DESCRIPTION OF THE PREFERRED EMBODIMENT

Figure 1:
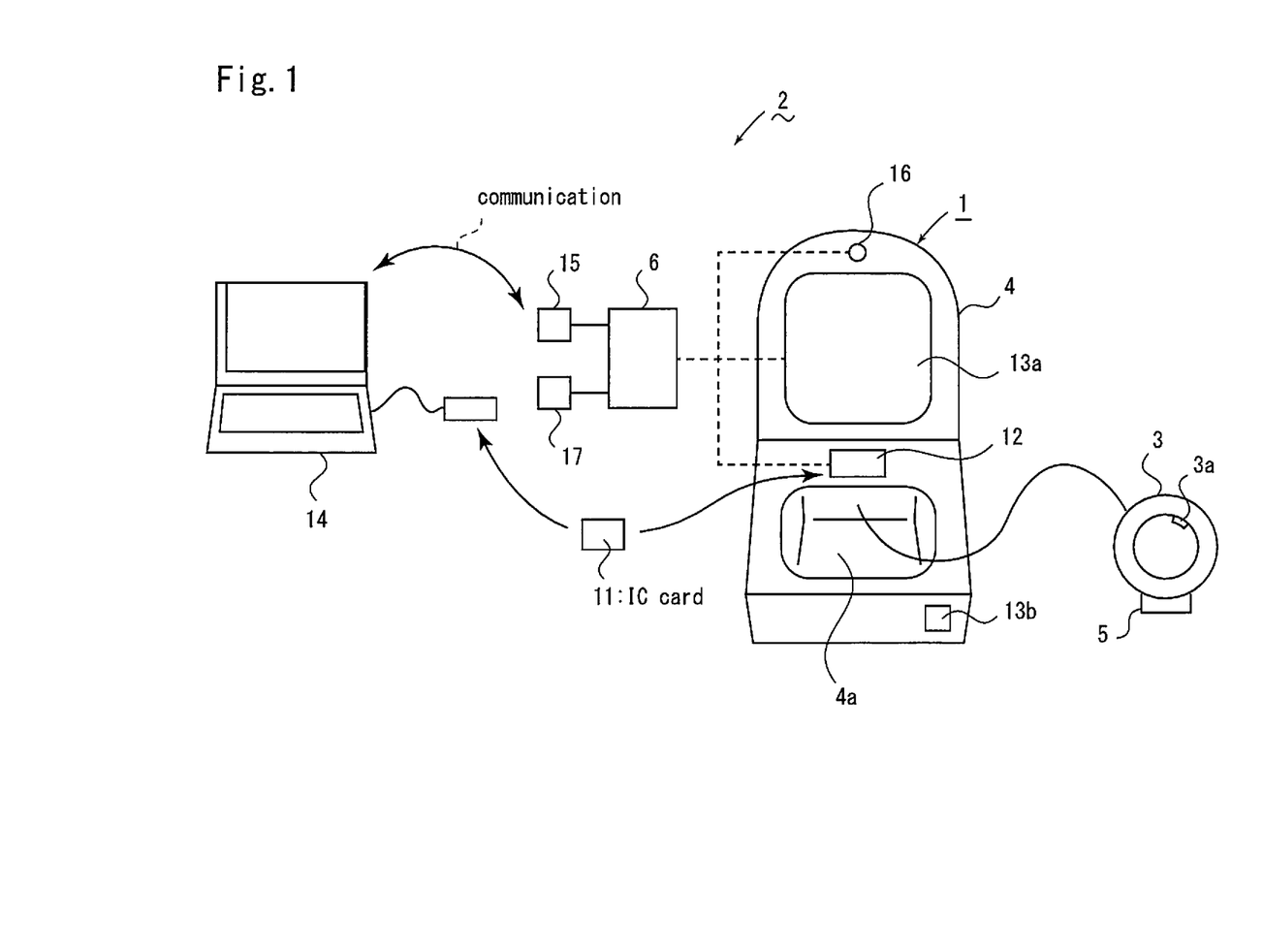
FIG. 1 is a configuration view of a phototherapeutic apparatus and a home treatment management system of the phototherapeutic apparatus according to the present embodiment.

The illustrated embodiment will be described below. FIG. 1 is a view for explaining a phototherapeutic apparatus 1 and a home treatment management system 2 using the phototherapeutic apparatus 1. The phototherapeutic apparatus 1 is an apparatus for treating skin diseases such as psoriasis, vitiligo, atopic dermatitis and the other refractory skin diseases. The phototherapeutic apparatus 1 is installed at the home of a patient so that the patient can treat his or her skin disease at home.

In the following description, the patient is also a user to perform the operation of the phototherapeutic apparatus 1. However, a person other than the patient, such as a nursing attendant who tends the patient, can also perform the operation, and when the phototherapeutic apparatus 1 is used in the medical institution, the doctor is the user.

The phototherapeutic apparatus 1 includes a probe 3 that can be held by the user, and a body 4 connected to the probe 3 through a cable. The body 4 is formed with a container 4a capable of receiving the probe 3, and the user can receive the probe 3 and other auxiliaries into the container 4a to easily carry the phototherapeutic apparatus 1. Note that the connection between the probe 3 and the body 4 is not necessarily wired, but may be one of various wireless systems.

The probe 3 is provided with a photo-irradiation unit 5 that irradiates the skin of the patient with light, which is a so-called narrow-band ultraviolet B (UVB) light emitted with the wavelength of 280 to 320 nm. Irradiating the affected part of the patient with the light at the above wavelength enables the treatment of the skin diseases as described above.

The probe 3 has a shape easy for the user to operate and includes a trigger switch 3a configured to instruct the start of irradiation with light from the photo-irradiation unit 5. The probe 3 also includes a cover, not illustrated, to prevent the light applied from the photo-irradiation unit 5 from being directly incident on the eye of the patient.

The body 4 is provided with a power supply part, not illustrated, that supplies power to the photo-irradiation unit 5, and a control unit 6 for controlling light beams applied from the photo-irradiation unit 5 based on the operation of the probe 3.

The control unit 6 performs the controls in accordance with set values of the irradiation output, irradiation time, irradiation frequency, and the like of the light beams applied from the photo-irradiation unit 5. When the trigger switch 3a of the probe 3 is operated, the control unit 6 causes the photo-irradiation unit 5 to perform irradiation with the light in accordance with these set values. Note that an irradiation amount, obtained by multiplying the irradiation output by the irradiation time, can also be represented as the set value.

In the case of treatment using such a phototherapeutic apparatus, conventionally, the doctor diagnoses an affected part of a patient in the medical institution and sets an appropriate irradiation output, irradiation time, irradiation frequency, and the like of the light beams to the phototherapeutic apparatus for each patient every time.

Then, the doctor brings the probe of the phototherapeutic apparatus into contact with the affected part and operates the trigger switch of the probe in that state, so that the affected part is irradiated with the light beams set by the control unit to treat the affected part.

The doctor sets the irradiation output and the like for the light on each affected part and operates the probe in the medical institution. However, when the phototherapeutic apparatus as thus described is installed at the home of the patient and the user who is the patient himself or herself, a nursing attendant, or some other person operates the phototherapeutic apparatus, it is necessary to eliminate an error in operation by the user to perform safe and reliable treatment.

That is, the user has difficulties in accurately positioning the probe, and even when the user can accurately position the probe on the affected part, the user has difficulties in setting an appropriate irradiation output and the like of the light for the affected part. When a plurality of affected parts which are different in terms of the irradiation output, irradiation time, and irradiation frequency are treated, the operation becomes more complex and can cause an error in operation.

Therefore, the following configuration has been provided in the phototherapeutic apparatus 1 of the present embodiment, whereby the phototherapeutic apparatus 1 enables the user, such as the patient himself or herself or the nursing attendant, to perform proper treatment based on the doctor's instruction First, in the probe 3, an operation switch and the like except for the trigger switch 3a are omitted to prevent the user from performing an unnecessary operation or an erroneous operation.

The body 4 is provided with: a read unit 12 that reads a treatment protocol registered in an IC card 11 and registers the read treatment protocol into the control unit 6; and a monitor 13a and a voice output part 13b as operation indication units that indicate a region to be irradiated with light beams, the region being registered in the read treatment protocol.

The IC card 11 is a mobile memory medium that the patient receives from the doctor in the medical institution. In the IC card 11, based on a diagnosis result, a treatment protocol is registered along with a region to be irradiated with the light, namely the position of the affected part, the treatment protocol having settings of set values made up of the irradiation output, irradiation time, irradiation frequency, and the like of the light beams applied from the photo-irradiation unit 5.

Then, the treatment protocol is read from the IC card 11 into the reader unit 12 and registered into the control unit 6. At this time, the user can register the treatment protocol into the control unit 6 just by touching the IC card 11 on the read unit 12, for example, without the need for any other operation.

Next, on the monitor 13a, an image indicating the region to be irradiated with the light is displayed based on the treatment protocol registered in the control unit 6. Specifically, an actual picture or video of the affected part, or animation or illustration instead of the actual picture or video, is displayed, and any display technique can be adopted so long as same enables clear recognition of the position to be touched with the probe 3. Further, the user is notified of the region to be treated with a voice from the voice output part 13b.

With such a configuration, the user can accurately position the affected part on the probe 3 while watching the image or the like displayed on the monitor 13a or by listening to the notification from the voice output part 13b. The user then operates the trigger switch 3a of the probe 3 in that state, and the control unit 6 causes the photo-irradiation unit 5 to perform irradiation with the light beams with an irradiation output, irradiation time, and irradiation frequency suitable for the affected part in accordance with the set values set in the treatment protocol, so that the affected part can be treated appropriately.

The treatment using the phototherapeutic apparatus 1 is effective when continuously performed over a predetermined period. However, when the affected part is irradiated with a large quantity of light beams for a short time, the treatment damages the affected part, and such irradiation is thus not desired.

Therefore, in the phototherapeutic apparatus 1 of the present embodiment, the interval of the irradiation with the light for each region to be irradiated is set in the treatment protocol registered in the control unit 6.

Accordingly, even when the user operates the phototherapeutic apparatus 1, until at least the time corresponding to the set interval elapses, the control unit 6 causes the monitor 13a to display the impossibility of re-treatment, and the light beams cannot be applied from the photo-irradiation unit 5.

The above body 4 is provided with: a communication unit 15 that communicates with a terminal 14 such as a personal computer provided in the medical institution, a smartphone, and a tablet; and a camera 16 that photographs an image of the state of the patient's skin. Further, the control unit 6 is provided with a protocol change unit 17 configured to change the content of the treatment protocol registered in the control unit 6.

The communication unit 15 transmits the image, photographed with the camera 16, to the terminal 14 in the medical institution, and the medical doctor can observe the state of the affected part of the patient by using the terminal 14.

The doctor diagnoses the affected part based on the image received at the terminal 14, to determine whether or not additional treatment is necessary for the affected part and to consider whether or not a change in the irradiation output, irradiation time, or irradiation/frequency of the light beams is necessary when a future treatment is to be performed.

Thereafter, when the number of times of treatment is to be changed or the set value of the light beams is to be changed, the doctor creates a new treatment protocol and transmits this treatment protocol as protocol change information that is based on the diagnosis result from the terminal 14 to the phototherapeutic apparatus 1 at the home of the patient via the communication unit 15.

At the home of the patient, when the communication unit 15 of the phototherapeutic apparatus 1 receives the protocol change information made up of the new treatment protocol, the protocol change unit 17 changes the treatment protocol, having been registered so far in the control unit 6, to the new treatment protocol.

Note that the camera 16 and the communication unit 15 can be replaced by a camera and a communication unit provided in a conventionally known mobile communication terminal, such as a smartphone or a tablet.

At the time of changing the treatment protocol registered in the control unit 6 to the new treatment protocol, it is possible to have short-range communications with the read unit 12 by using the function of the mobile terminal and causing the read unit 12 to read the new treatment protocol.

In addition, it is also conceivable that an encryption code for rewriting the treatment protocol is registered in the protocol change unit 17 in advance, and an input unit provided in the body 4 inputs the encryption code transmitted as the protocol change information from the medical institution to the mobile terminal, thereby changing the treatment protocol.

That is, while it is possible to change the treatment protocol by transmitting a new set value as the protocol change information and by the user of the phototherapeutic apparatus 1, such as the patient or the nursing attendant, directly inputting the new set value, it is also possible to change the treatment protocol currently in use by previously registering into the protocol change unit 17 a plurality of change commands for the set values, such as a decrease or an increase in irradiation output by several percent, and reading a corresponding change command in accordance with an encryption code that is input.

In the following, a treatment procedure for skin diseases at home by using the phototherapeutic apparatus 1 and the home treatment management system 2 with the above configuration will be described with reference to FIGS. 2 to 4.

Figure 2:
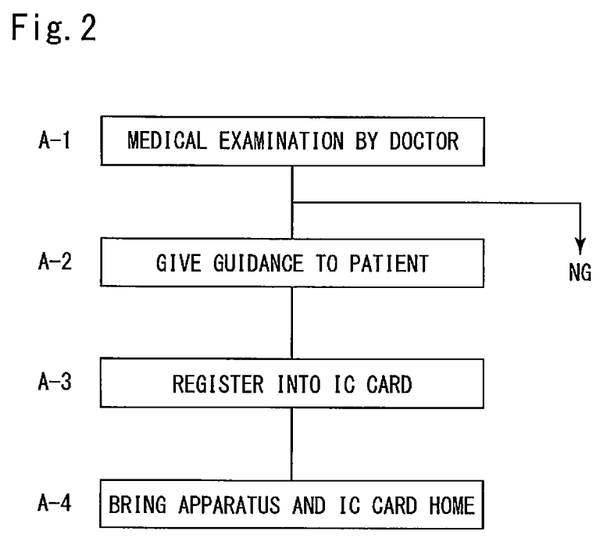
FIG. 2 is a flowchart illustrating a procedure of home treatment using the phototherapeutic apparatus in the medical institution.

First, FIG. 2 illustrates a procedure in the medical institution, and the patient is firstly given a medical examination by the doctor in the medical institute (A-1). Based on the state of the affected part of the patient, the doctor determines whether or not home treatment using the phototherapeutic apparatus 1 is possible.

Next, when the doctor determines that home treatment is possible, the doctor gives guidance to the user such as the patient or the nursing attendant, concerning an operation method and usage precautions for the phototherapeutic apparatus 1, and the like (A-2).

Then, based on the contents of the diagnosis, the doctor creates a treatment protocol in which an irradiation output, irradiation time, and irradiation frequency of light are set for each region to be irradiated with the light, and registers the created treatment protocol to the IC card 11 (A-3).

The patient then receives the phototherapeutic apparatus 1 together with the IC card 11 from the medical institution and brings those home (A-4).

Figure 3:
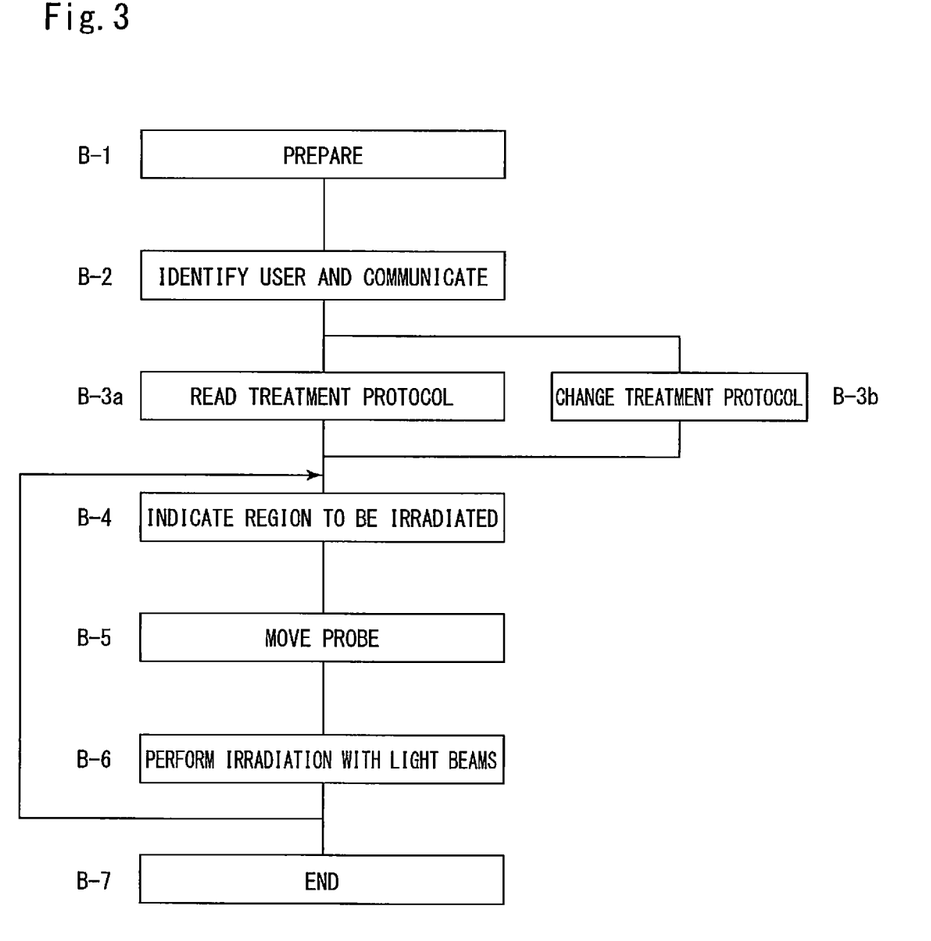
FIG. 3 is a flowchart illustrating the procedure of the home treatment using the phototherapeutic apparatus at home.

FIG. 3 illustrates a treatment procedure at home. First, the user makes preparation such as connecting the body 4 of the phototherapeutic apparatus 1 to the power supply and connecting the probe 3 to the body 4 through the cable (B-1).

When activating the phototherapeutic apparatus 1, the user first touches the IC card 11 received from the medical institution on the reader unit 12 of the body 4 and inputs a password or the like to confirm that the user is the patient to be given treatment with the apparatus. The communication unit 15 is also activated to communicate with the terminal 14 of the medical institution and confirm whether or not there has been a change in the treatment protocol (B-2).

When this home treatment is the first time of treatment and there has been no change in the treatment protocol, the read unit 12 of the body 4 is caused to read the treatment protocol registered in the IC card 11 (B-3a).

As a result, the treatment protocol registered in the IC card 11 is registered into the control unit 6. When this treatment is the second time of treatment or after and there has been no change in the treatment protocol, it is possible to omit the reading of the treatment protocol and use the treatment protocol registered in the control unit 6 as it is.

On the other hand, when the treatment protocol has been changed as a result of the diagnosis by the doctor using the communication unit 15, illustrated in FIG. 4 described later, the communication unit 15 receives a new treatment protocol transmitted from the terminal 14 of the medical institution, and the protocol change unit 17 changes the treatment protocol registered in the control unit 6 to the new treatment protocol (B-3b).

As one example of the treatment protocol, for example, the following settings are made for irradiation of the face as the region to be irradiated: in a first week, the irradiation is performed every other day with an irradiation output of 20 mW/cm$^2$, an irradiation time of five seconds, and an irradiation frequency of two; in a second week, the irradiation is performed every day with an irradiation output of 20 mW/cm$^2$, an irradiation time often seconds, and an irradiation frequency of one; and in a third week, the irradiation is performed every day with an irradiation output of 20 mW/cm$^2$, an irradiation time of 15 seconds, and an irradiation frequency of one.

Further, the following settings are made for irradiation of the left arm as the region to be irradiated: in the first week, the irradiation is performed every day with an irradiation output of 20 mW/cm$^2$, an irradiation time of ten seconds, and an irradiation frequency of one; in the second week, the irradiation is performed every day with an irradiation output of 30 mW/cm$^2$, an irradiation time of five seconds, and an irradiation frequency of two; and in the third week, the irradiation is performed every day with an irradiation output of 30 mW/cm$^2$, an irradiation time of ten seconds, and an irradiation frequency of one.

When the treatment protocol is to be changed to the new treatment protocol as a result of the diagnosis, for example, as a result of the diagnosis at the point in time of completion of the irradiation of the face as the region to be irradiated in the first week, it is possible to change the settings to the following: in the second week, the irradiation is performed every day with an irradiation output of 20 mW/cm$^2$, an irradiation time of five seconds, and an irradiation frequency of one; and in the third week, the irradiation is performed every day with an irradiation output of 20 mW/cm$^2$, an irradiation time of 10 seconds, and an irradiation frequency of one, while not changing the settings for the left arm as the region to be irradiated.

Subsequently, based on the treatment protocol registered in the control unit 6, the monitor 13a and the voice output part 13b indicate the region to be irradiated with the light beams by the probe 3 (B-4). Specifically, based on the treatment protocol, an image showing the affected part as the region to be irradiated is displayed on the monitor 13, while the user is notified of the affected part with a voice.

Next, the user holds the probe 3 and positions the probe 3 on the affected part (the region to be irradiated) displayed on the monitor 13a (B-5).

For example, a sensor or the like is provided in the probe 3 in advance for safety's sake, so that the control unit 6 can cancel the operation of the trigger switch 3a until the contact of the probe 3 with the skin is detected.

Subsequently, the user operates the trigger switch 3a provided on the probe 3 to irradiate the affected part with light from the photo-irradiation unit 5 (B-6). When the user operates the trigger switch 3a, the control unit 6 causes the photo-irradiation unit 5 to irradiate the affected part with the light in accordance with the irradiation output, irradiation time, and irradiation frequency of the light which are registered in the treatment protocol and correspond to the region to be irradiated.

In a case where the patient performs the irradiation by himself or herself or some other cases, by switching the display of the monitor 13a from the image showing the region to be irradiated to an image being currently photographed with the camera 16, it is possible to perform the irradiation while confirming the region to be irradiated by using the image, and when the face as the region to be irradiated is treated, it is possible to irradiate an affected part necessary for the irradiation while confirming on the monitor 13a the actual face of the patient being photographed with the camera 16, as if the patient is using a mirror.

Upon completion of the irradiation with the light based on the treatment protocol in the manner as described above, the treatment of the affected part is completed, and the control unit 6 confirms whether or not other affected parts need to be treated.

When the other affected parts need to be treated, the control unit 6 repeats the operations related to B-4, B-5, and B-6 above until completion of treatments of all the other affected parts, and completes the treatments concerning all the treatment protocols registered in the IC card 11.

When the treatments of all the affected parts are completed, an image diagnosis procedure (FIG. 4) is performed by the doctor using the communication unit 15. When the diagnosis is unnecessary, the power supply of the phototherapeutic apparatus 1 is cut off, and the probe 3 and the like are put away (B-7).

Note that the doctor can also use the phototherapeutic apparatus 1 as configured above in the medical institution. That is, the IC card 11 is prepared for each patient to be treated, a treatment protocol for each patient is registered in advance into each IC card 11, and at the time of treatment in the medical institution, the treatment protocol is read from the IC card 11 corresponding to the target patient. This enables the doctor to save the labor of inputting a treatment protocol at each time of treatment and prevent input errors.

Figure 4:
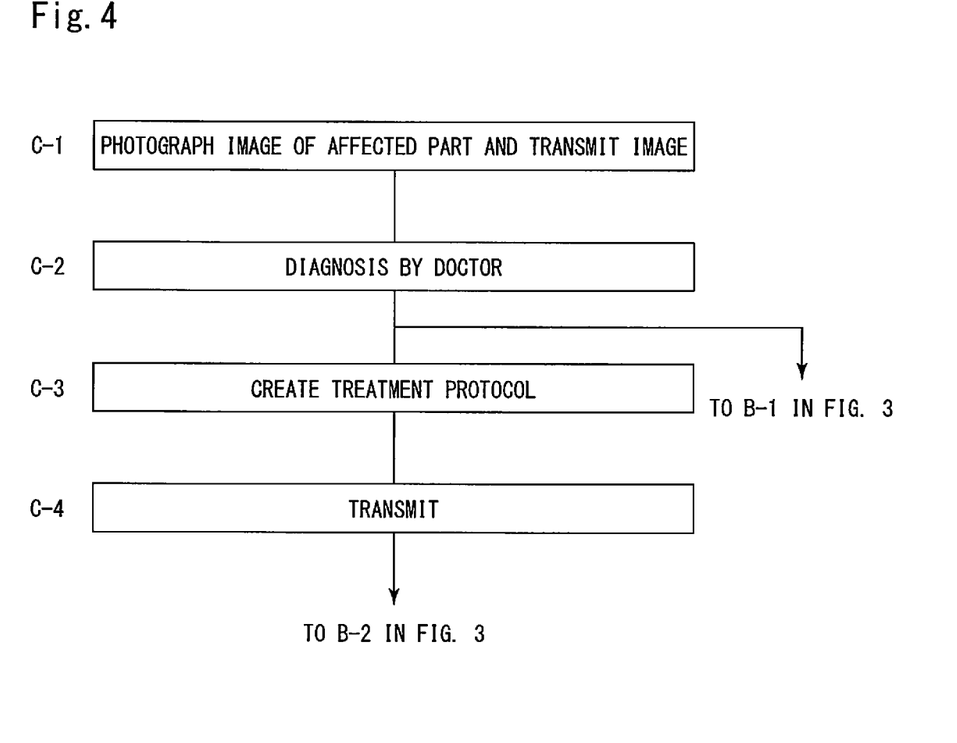
FIG. 4 is a flowchart illustrating the procedure to change the treatment protocol of the home treatment using the phototherapeutic apparatus.

FIG. 4 is for explaining the procedure to change the treatment protocol which is made, after completion of the treatment with the phototherapeutic apparatus 1, based on the doctor's diagnosis using an image of the affected part that has completed the treatment and based on the diagnosis result.

First, when the treatment with the phototherapeutic apparatus 1 is completed based on the procedure illustrated in FIG. 3, the user photographs an image of the affected part, having completed the treatment, with the camera 16 provided in the body 4 and transmits the image to the terminal 14 of the medical institution by using the communication unit 15 (C-1). When a plurality of affected parts are treated at this time, the user transmits the images of all the affected parts or the images of the affected parts having changed due to irradiation.

In the medical institution, the terminal 14 receives the image, and the doctor diagnoses the state of the affected part based on the received image (C-2). The doctor determines, based on the image of the affected part, whether further treatment is necessary or a change in the setting of the light beams for irradiation is necessary.

When determining as a result of the diagnosis that the treatment will be continued with the treatment protocol used so far, the doctor performs no particular operation, and the user can continue the treatment based on the operation illustrated in FIG. 3.

On the other hand, when the doctor determines as a result of the diagnosis that further treatment is not necessary or a change in the setting of the light for irradiation is necessary, the doctor creates a new treatment protocol for the corresponding affected part (C-3).

Specifically, the doctor deletes the treatment protocol for the affected part that no longer needs the treatment, or creates a treatment protocol with new set values in which the irradiation output and the irradiation time of the light beams are increased or decreased based on the state of the affected part after the treatment.

Upon creation of the new treatment protocol in such a manner, the doctor operates the terminal 14 to transmit the new treatment protocol and an encryption code as the protocol change information to the phototherapeutic apparatus 1 of the patient (C-4).

As described in the process of B-2 in FIG. 3 above, when the phototherapeutic apparatus 1 is activated, the communication unit 15 receives the created treatment protocol with the new set values. Then, in the process of B-3b in FIG. 3, the protocol change unit 17 reads the new treatment protocol instead of the treatment protocol previously read in the control unit 6 to perform rewriting, or the user inputs the new treatment protocol.

According to the phototherapeutic apparatus 1 of the present invention, the user such as the patient himself or herself or the nursing attendant can accurately perform the treatment using the light beams in accordance with the treatment protocol created based on the doctor's diagnosis.

At that time, the affected part is automatically irradiated with the light beams in accordance with the set value suitable for the affected part by the user just operating and positioning the probe 3 on the affected part based on the indications of the monitor 13a and the voice output part 13b and operating the trigger switch 3a in that state. Hence it is possible for the user, if not a doctor, to perform the phototherapy at the set value suitable for the affected part, without causing a wrong location to be irradiated with the light beams.

In the above embodiment, the case where the phototherapeutic apparatus 1 is provided with the communication function has been described. In the case of the usage method where the mobile terminal transmits an image as described above, it is possible to change the treatment protocol as in the above embodiment in the following manner: in the step of B-3b, the user, such as the patient or the nursing attendant, by himself or herself inputs the encryption code and the new set value transmitted from the doctor to the mobile terminal by the step of C-4.

What is claimed is:

1. A phototherapeutic apparatus comprising:
    a probe held and operated by a user;
    a photo-irradiation unit that is provided in the probe and irradiates an affected part with light beams; and
    a body provided with a control unit that controls the light beams of the photo-irradiation unit, the body comprising:
        a read unit that reads a treatment protocol registered in a mobile memory medium; and
        an operation indication unit that indicates to a user a region to be irradiated with the light beams, the region being set in the treatment protocol;
    wherein the control unit causes the operation indication unit to indicate the region to be irradiated and causes the photo-irradiation unit to perform an irradiation treatment with the light beams at an irradiation amount set in the treatment protocol, and the control unit causes the operation indication unit to indicate an impossibility of re-treatment and prevents the photo-irradiation unit from performing an irradiation treatment with the light beams again until a set time interval between irradiation treatments elapses.

2. The phototherapeutic apparatus according to claim 1, wherein:
    the phototherapeutic apparatus comprises a monitor that serves as the operation indication unit; and
    the region to be irradiated is indicated to the user with an image.

3. The phototherapeutic apparatus according to claim 1, wherein:
    the phototherapeutic apparatus comprises a voice output unit that serves as the operation indication unit; and
    the region to be irradiated is indicated to the user with a voice from the voice output unit.

4. The phototherapeutic apparatus according to claim 1, wherein the control unit is provided with a protocol change unit that changes a set value of the treatment protocol.

5. The phototherapeutic apparatus according to claim 4, wherein:
    the phototherapeutic apparatus comprises a communication unit that transmits an image showing a state of the affected part to a terminal provided in a medical institution and receives protocol change information from the terminal of the medical institution; and
    the protocol change unit changes the set value of the treatment protocol based on the protocol change information.

* * * * *